United States Patent [19]

Schneider et al.

[11] Patent Number: 5,192,318
[45] Date of Patent: Mar. 9, 1993

[54] ONE-PIECE BIFOCAL INTRAOCULAR LENS CONSTRUCTION

[76] Inventors: Richard T. Schneider, 17 Alachua Highlands, Alachua, Fla. 32615; Richard H. Keates, 456 W. 10th Ave., Columbus, Ohio 43210

[21] Appl. No.: 928,141

[22] Filed: Aug. 11, 1992

Related U.S. Application Data

[63] Continuation of Ser. No. 561,256, Jul. 30, 1990, abandoned, which is a continuation of Ser. No. 297,966, Nov. 17, 1989, abandoned, which is a continuation-in-part of Ser. No. 182,253, Apr. 15, 1988, abandoned, which is a continuation-in-part of Ser. No. 15,878, Feb. 18, 1987, abandoned, which is a continuation-in-part of Ser. No. 871,077, Jun. 5, 1986, abandoned.

[51] Int. Cl.$^5$ ............................................. A61F 2/16
[52] U.S. Cl. ........................................................ 623/6
[58] Field of Search ............................................ 623/6

[56] References Cited

U.S. PATENT DOCUMENTS

| | | |
|---|---|---|
| 3,034,403 | 5/1962 | Neefe . |
| 3,037,425 | 6/1962 | De Carle . |
| 3,270,099 | 8/1966 | Camp . |
| 3,279,878 | 10/1966 | Long . |
| 3,794,414 | 2/1974 | Wesley . |
| 4,010,496 | 3/1977 | Neefe . |
| 4,373,218 | 2/1983 | Schachar . |
| 4,402,579 | 9/1983 | Paler . |
| 4,435,856 | 3/1984 | L'Esperance . |
| 4,450,593 | 5/1984 | Paler . |
| 4,451,938 | 6/1984 | Kelman . |
| 4,466,858 | 8/1984 | Paler . |
| 4,473,434 | 9/1984 | Paler . |
| 4,504,982 | 3/1985 | Burk . |
| 4,512,040 | 4/1985 | McClure . |
| 4,525,043 | 6/1985 | Bronstein . |
| 4,619,657 | 10/1986 | Keates et al. . |
| 4,636,211 | 1/1987 | Nielsen ................................. 623/6 |
| 4,666,446 | 5/1987 | Koziol et al. . |
| 5,026,396 | 6/1991 | Darin ..................................... 623/6 |
| 5,089,024 | 2/1992 | Christie et al. ........................ 623/6 |

FOREIGN PATENT DOCUMENTS

| | | |
|---|---|---|
| 0140063 | 5/1985 | European Pat. Off. ................ 623/6 |
| 2510768 | 4/1983 | France . |
| 8603961 | 7/1986 | World Int. Prop. O. .............. 623/6 |

OTHER PUBLICATIONS

"Ultrafocal Bifocal Contact Lens" Claud A. Kendall, O.D, Pub. 623-6, Jan. 1976, pp. 31-35.
Science & Technology, "Bifocal Contact Lenses without a pain in the Neck."
"Clinical Results of the Multifocal Lens", *J. Cataract Refract Surg*, vol. 13, Sep. 1987, pp. 557-560.

*Primary Examiner*—Randall L. Green
*Assistant Examiner*—D. Willse
*Attorney, Agent, or Firm*—Merchant, Gould, Smith, Edell, Welter & Schmidt

[57] ABSTRACT

A rigid bifocal intraocular lens (60) for use as an artificial lens implant is disclosed. In one embodiment, the intraocular lens has a rigid lens body (61) having a chord (61a) and first and second lens portions (62) and (63). The first lens portion (61) has a focal length and the second lens portion (63) has a focal length different from the focal length of the first lens portion (62). The first lens portion (62) is positioned on one side of the chord (61a) and the second lens portion (63) is positioned on the other side of the chord (61a). The first and second lens portions (62 and 63) form an integral, one-piece optical lens body (61) with the first and second lens portions being non-movable with respect to one another. In another embodiment the rigid lens body has a first central circular lens portion and a second outer annular lens portion. In a preferred form of this embodiment the inner, circular lens has a diameter of a between about 1.8 millimeters and about 2.0 millimeters, with the outer annular lens portion having a diameter of between about 6 millimeters and 7 millimeters. A preferred corrective power for the lenses used in the above-referenced embodiments is between about +15 and about +25 diopters for a distance-viewing lens portion, and a corrective power for a near-viewing portion of between about +3 and +4 diopters greater than the corrective power of the distance-viewing portion. Preferably, the lens portions are formed from molding in a manner avoiding introduction of any substantial refractive index gradient in the lens material.

3 Claims, 3 Drawing Sheets

FIG. 4
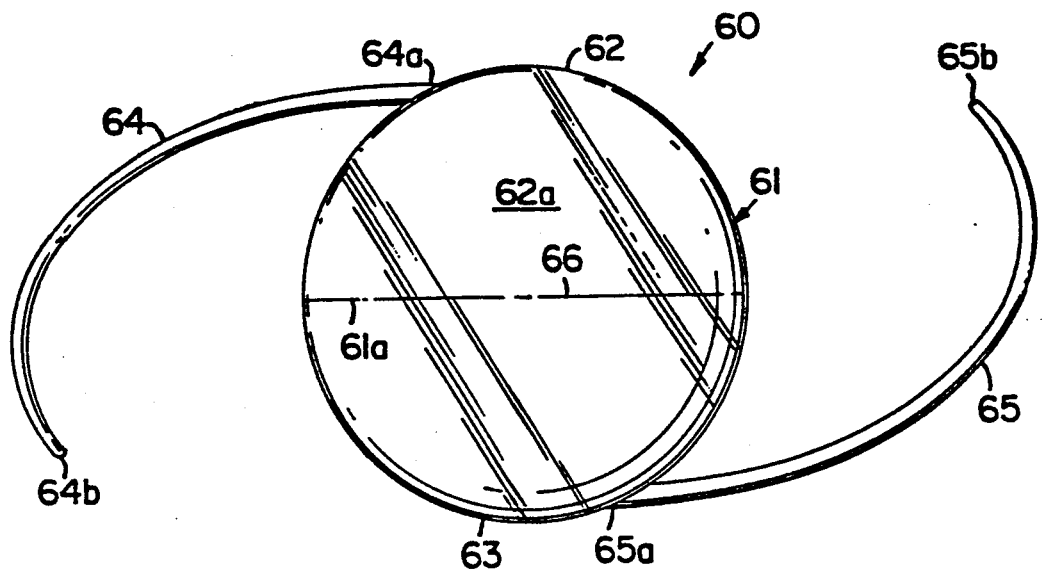
FIG. 5
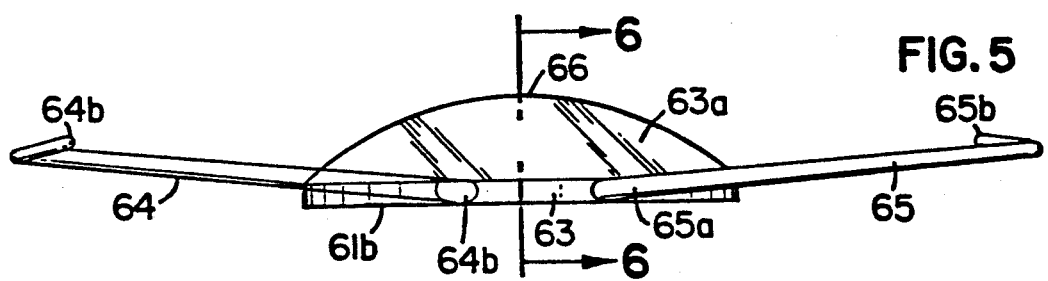
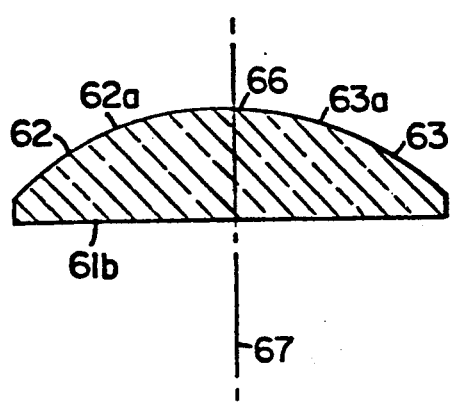
FIG. 6

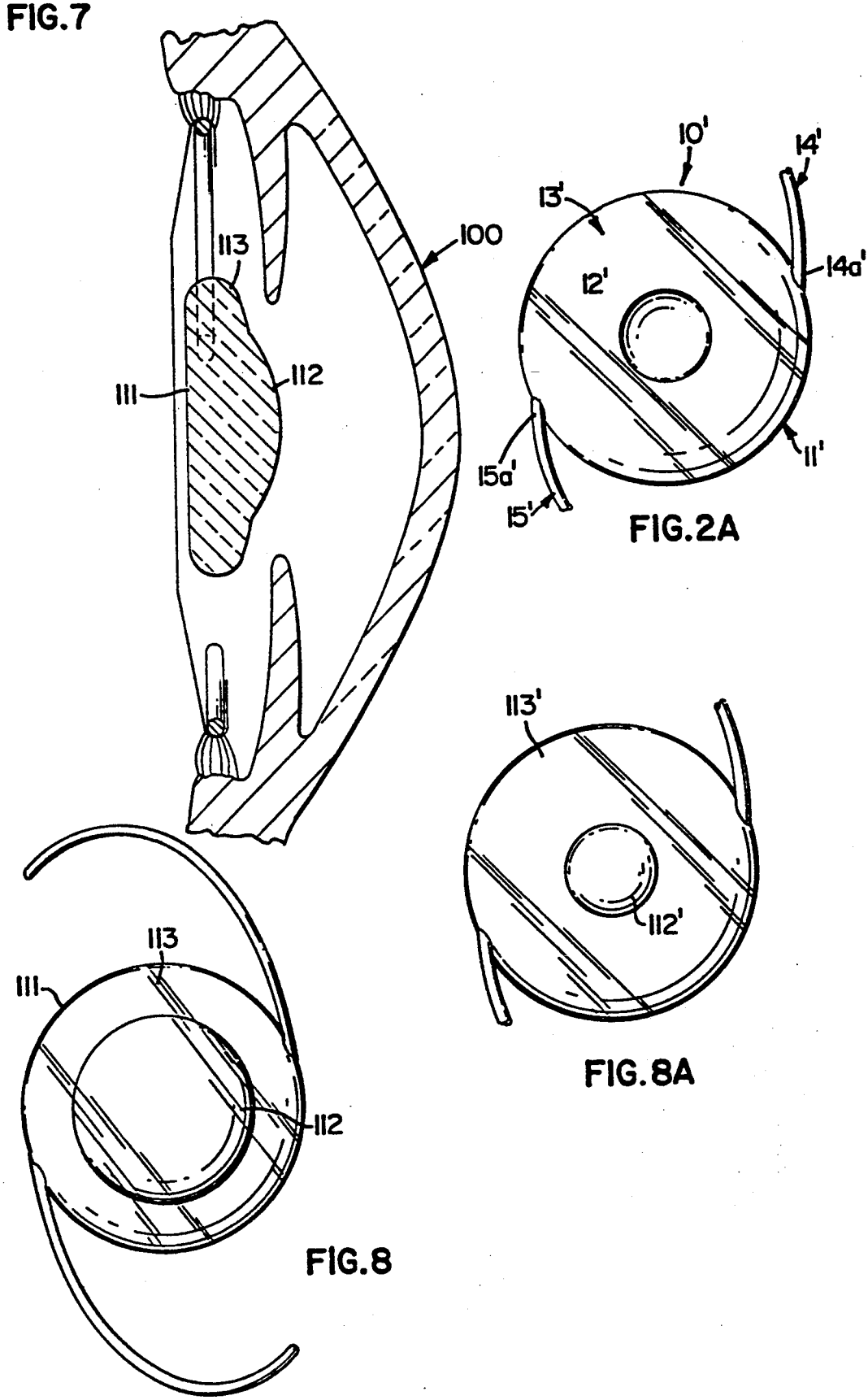

ONE-PIECE BIFOCAL INTRAOCULAR LENS CONSTRUCTION

This application is a continuation application of Ser. No. 07/561,256, filed Jul. 30, 1990, now abandoned, which is a continuation of Ser. No. 07/297,966, filed Jan. 17, 1989, now abandoned, which is a continuation-in-part of Ser. No. 07/182,253, filed Apr. 15, 1988, now abandoned, which is a continuation-in-part of Ser. No. 07/015,878, filed Feb. 18, 1987, now abandoned, which is a continuation-in-part of Ser. No. 06/871,077, filed Jun. 5, 1986, now abandoned.

BACKGROUND OF THE INVENTION

1. Field of the Invention

This invention relates generally to intraocular lenses to be used as artificial lens implants in eyes from which the cataractous natural lens has been removed, and more particularly to an improved rigid lens having multiple lenses.

2. Description of the Prior Art

The implantation of an intraocular lens for restoring vision after cataract surgery is well-known in the art. In general, two forms of surgery are used to remove cataracts. These are extracapsular cataract extraction and intracapsular extraction. (Discussed in Hoffer U.S. Pat. Re. 31,626.) Following extraction of a cataractous lens, an intraocular lens is normally implanted in either the anterior or the posterior chamber of the eye. In an anterior chamber implant, the lens is generally situated forward of, or mounted to, the iris. In the case of posterior chamber implants, the lens is situated behind the iris and may be mounted within the cleft or fornix of the capsule which remains in place after extracapsular surgery. Posterior chamber implants are generally preferred, in part because this is the location from which the natural lens is removed.

In both anterior or posterior chamber implants, the lens is usually centered and fixed in position by one or more supporting strands or haptic members. While available intraocular lenses incorporate haptic member(s) having various geometric shapes and configurations, the typical haptic member is a flexible strand of nonbiodegradable material which is fixed to the lens body, and exhibits specific spring-like memory qualities so that the haptic member can be compressed or off-set from the normal rest position and thereafter returned to the fully extended condition when pressure is removed.

The intraocular implant is an artificial lens which has one given focal length. Since the intraocular implant is made of a rigid material it cannot change the focal length by deformation as the natural lens does (called accommodation). As a result of this, if the focal length is selected to provide a sharp image for a distant object, then an object which is closer (i.e. at reading distance) will not be imaged sharply on the retina. Alternately, one could image closer objects sharp by selecting a different focal length, but then, of course, distant objects would appear out of focus.

Contact lenses have been made having multi-focal lengths and also having variable light absorption. R. N. Camp U.S. Pat. No. 3,270,099 issue Aug. 30, 1966 discloses a method for making a multi-focal length contact lens. The Camp patent deals with a contact lens which is not used for the same function or manner as an intraocular lens. Further, the Camp patent teaches that the eye uses the inner part of the cornea for near vision while the outer part is used for distant vision. For this reason, the Camp contact lens covers the cornea with a contact lens which has one power in the inner part and another power in the outer part. As a basis for such a lens, the Camp patent teaches that the divergent rays which enter the peripheral portion are not focused on the retina and hence are unseen. This is, of course, a violation of the laws of physics as light is detected by the retina regardless of whether it is focused or unfocused.

Neefe U.S. Pat. No. 3,034,403 was issued May 15, 1962 and discloses a contact lens of apparent variable light absorption. The center portion of the contact lens is tinted while the outer portion is clear.

Bifocal intraocular lenses are known, see for example Nielson et al U.S. Pat. No. 4,636,211. The Nielson reference discloses a concentrically bifocal (or target) lens, i.e. a lens implant having an outer annular portion of one power, in an inner circular portion of another power. The add on power difference between the far and near vision portions of Nielson et al '211 is indicated as being +2.50 diopters. The inner lens of Nielson et al '211 is indicated as being, on the average, about 2.12 mm in diameter.

The features that are possible in a bifocal intraocular lens are, to a great extent, dependent upon the method of manufacture used and/or the material from which the lens is made. A conventional method of making an intraocular lens, is through the compression molding technique. For this technique, a mold is made by machining a cavity out of a piece of tool steel. The radius of curvature of the cavity is made equal to the radius of curvature of the convex side of the lens. The cavity is then polished. Material for the lens, which typically has a consistency analogous to plexiglass, is generally manufactured in the form of rods preferably having an outside diameter equal to that of an intraocular lens be produced in the mold. The material of the rod is cut into small discs, which are heated and pressed in the polished mold. After cooling, the formed lens is released from the mold. Generally, the obtained product is ready for implantation, without any further manipulations, except typically for sterilization. In many instances haptics will also have been added.

Bifocal intraocular lenses can be formed as a gradient index lenses. That is, they are constructed to have a refractive index gradient through the optical region, with the gradient providing for different powers. There are basically two conventional ways of achieving this. A first is to produce the implant as a conventional implant, as previously described. The finished product, as a unifocal IOL, is then provided with a hole drilled in the center. With a second compression mold, a cylinder with one planar end and one spherical end, whereby the spherical end has a radius of curvature equal to the radius of the curvature of the IOL having a hole drilled therein, is formed. The obtained cylinder is inserted into the bore hole of the first lens, producing a lens with a smooth outer surface. The materials chosen for the first lens (with a hole in the center) in the second cylinder (the inner lens) are typically sufficiently different, so that the refractive indices of the two differ enough to cause a desired bifocal arrangement.

Another conventional way to produce a gradient index IOL is to start with lens material in rod form. The rod then is heated from the outside, preferably with infrared radiation, to heat the material unevenly. In particular, the outside is heated more than the inside.

The induced stresses change the material's refractive index slightly, and provide a gradually changing refractive index from the outside through to the inside. After this treatment, the rod is cut into discs, and the individual discs are polished. In principle, the discs could be flat (planar) on both sides. However, typically the induced grading is not sufficient, so a curvature on the outer surface is needed to form a lens of appropriate power.

While the two methods of preparing a bifocal intraocular lens described are possible, neither is fully desirable as a method of producing a high quality bifocal intraocular lens.

The first method described can be used to produce a bifocal lens having an appropriate resolving power. However, the wall of the internal cylinder (i.e. the surface of interface between the two sections) will tend to produce reflection for certain angles of incidence. This will be perceived, by the wearer, as an undesirable glare. Also, an adhesive must, typically, be used for gluing the internal cylindrical portion in position. Such an adhesive may be subject to leaching in time, which can lead to further ocular problems.

The second method described is generally relatively expensive and difficult, and is not readily subject to precise control. In particular, with the method it can be difficult to precisely develop a desired gradient.

The present invention addresses many of the problems associated with prior art intraocular lenses, especially in that they have not provided for readily obtainable, rigid multi-focal length lens. The present invention provides for such a multi-focal length intraocular lens.

SUMMARY OF THE INVENTION

The present invention is a rigid bifocal intraocular lens adapted for use as an artificial lens implant. A single rigid implant is provided having one or more additional lenses ground into it, so as to function like bifocal glasses.

In the preferred embodiment a plurality of lens portions are formed in the intraocular lens and each lens portion is substantially non-movable with respect to the other(s).

The intraocular lens of the first embodiment has an optical lens body with a central, circular, lens portion and an outer, annular, lens portion. The central, or first, lens portion has a focal length and the second, or outer, annular lens portion has a focal length different from the focal length of the first lens portion. The relative areas of the two lens portions may vary, however in the first embodiment described the two are about the same size. Preferably the diameter of the outer annulus is about 6-7 millimeters, whereas the overall diameter of the inner circular lens portion is between about 1.8 and about 2.2 millimeters. Most preferably the diameter of the inner lens is less than about 2.0 millimeters. In general, it is desirable to make the inner lens less than 2.0 mm, since the effective diameter of the outer lens can be reduced by the iris. Thus, by turning up the intensity of the reading light, and causing the iris to constrict, a user of a bifocal intraocular lens according to the first embodiment can decrease the amount of light directed through the outer lens portion, leaving a (relatively) brighter near vision image for the brain to preferentially select and use. A theoretical smallest diameter for the inner lens portion, of about 1.0 mm, is possible, since in general a brain requires having similar intensities on at least six receptors, before it will accept a receptor output as it picks out. However, most person's iris' would not contract to this small a diameter.

The relative corrective powers of the lens portions may also vary; however, preferably, the corrective factor of the outer (annular) lens portion is between about +5 and +25 diopters, whereas the corrective power of the inner portion is between about +2 and +4 diopters larger than the power of the annular portion. More preferably the inner portion preferably has a corrective or add factor of between +3 and +4 diopters with respect to the outer portion. It has been observed that an add on of less than about +3 diopters is not completely desirable since it will not focus, unless the lens is placed in the anterior chamber, and implant is preferred in the posterior chamber. Also, such a small add on does not in general produce sufficiently different near and distance images for the brain to readily distinguish. Rather, with an add on less than +3 diopters, edge portions of the near vision portion will appear fuzzy. Most preferably, the add on is at least about +3.5 diopters. At this level clear, sharp, images from both lenses are generally discernable. In some instances, add-ons of greater than +4.0 diopters may be desirable and useful.

The first and second lens portions preferably form an integral, one-piece, bifocal optical lens body. A preferred method of formation has been found, which avoids the prior art and which yields an advantageous construction. In general, the method involves preparing a mold by pre-machining a cavity out of a piece of tool steel, to a radius of curvature approximately equal to the curvature of the convex part of the lowest power (for the preferred embodiment, the outer annular) lens. After this initial pre-machining of the mold, the radius of curvature for the lens portion having the highest power (for the preferred embodiment the inner lens) is machined and polished. The polished surface is then protected with a sealer, such as a wax. Then the radius of curvature of the lower power lens (for the preferred embodiment the outer lens) is precisely machined and polished into the mold. Since this radius is larger than the one previously cut, the part of the mold which was machined first is not disturbed. The wax cover protects against damage during a final polishing process. A bifocal lens can be readily made, by molding lens material in the mold.

In this manner, a bifocal intraocular lens which is not a gradient index lens, is readily manufactured. A high degree of precision can be obtained, in a relatively inexpensive manner.

The intraocular lens of an alternate embodiment has an optical lens body having a chord and first and second lens portions. The first lens portion has a focal length and the second lens portion has a focal length different from the focal length of the first lens portion. The first lens portion is positioned on one side of the chord and the second lens portion is positioned on the other side of the chord. The first and second lens portions form an integral, one-piece, bifocal optical lens body wherein the first and second lens portions are substantially non-movable with respect to one another. Preferably, for the alternate embodiment the lens body is substantially circular and the chord is a diameter of the lens body.

Intraocular lenses according to this alternate embodiment, can be readily manufactured using an analogue of the previously described preferred manufacturing process. In particular, the portion of the lens mold having the shortest radius of curvature machined, polished, and then protected with wax. Next, the portion of the lens mold having the highest radius of curvature, would be formed and polished. The lens can be readily made, by then molding leads material in more or less conventional manner.

For best results, the images from both lens portions for either embodiment should end up in the same plane. That is, the powers of the two lens portions should be selected so that the image from infinity projected through the second lens portion will be focused in about the same plane as the image from a close object being located at standard reading distance projected through the first lens portion. As a result of this construction, when a user wearing the intraocular implant uses same to view, both of the first and second lens portions may produce images substantially superimposed on one another. Depending on the distance to the object(s) being viewed and the amount of light present, one of the images will appear sharp and the other sufficiently defocused to permit the user's brain to select the sharper image for evaluation.

BRIEF DESCRIPTION OF THE DRAWINGS

FIG. 2A is generally the same as FIG. 2, except FIG. 2A is reduced, is fragmentary, and shows different relative sizes between various lens portions.

FIG. 4 is a top plan view of a second embodiment of the present invention.

FIG. 5 is a side elevational view of the lens shown in FIG. 4.

FIG. 6 is a cross-sectional view, taken along the line 6—6 of FIG. 4.

FIG. 7 is a cross-sectional view, of the eye and shows a lens incorporating an embodiment of our present invention implanted in the posterior chamber of the eye; the lens being a plano-convex variation of the embodiment shown in FIG. 1.

FIG. 8 is a top plan view of the lens of FIG. 7.

FIG. 8A is generally the same as FIG. 8, except FIG. 8A is reduced, is fragmentary, and shows different relative sizes between the various lens portions.

DETAILED DESCRIPTION OF THE INVENTION

Figure 1:
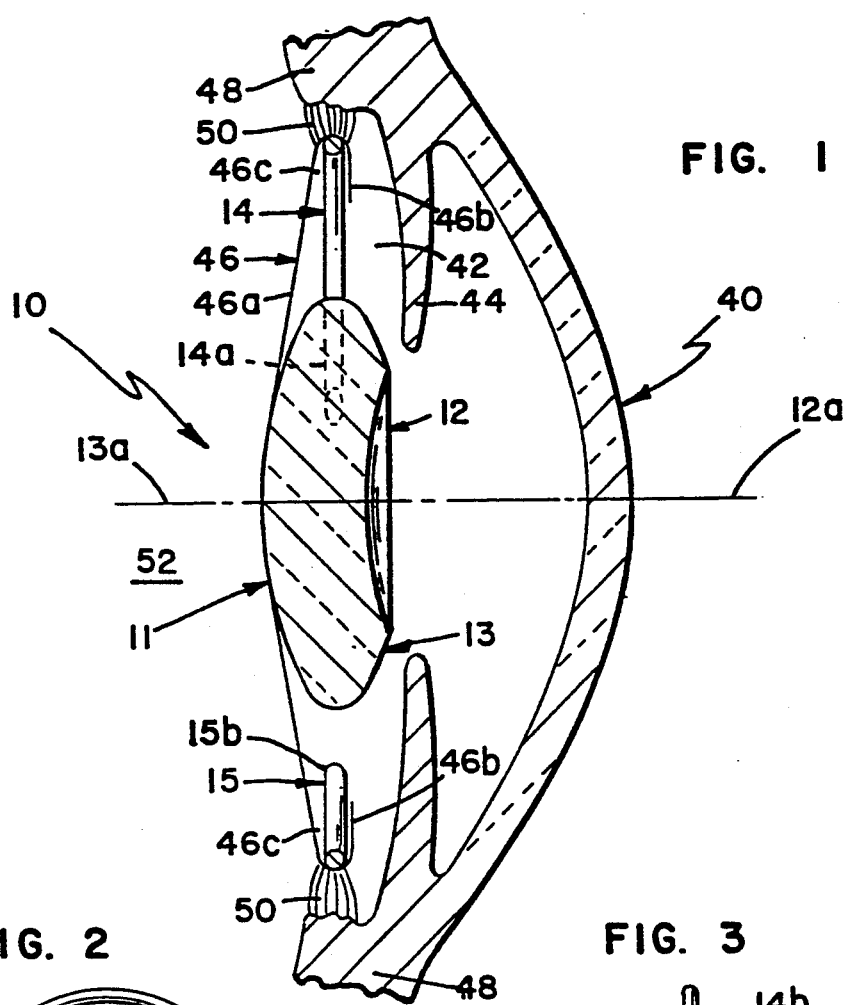
FIG. 1 is a cross-sectional view of the eye and shows a lens incorporating our present invention implanted in the posterior chamber of the eye.
Figure 2:
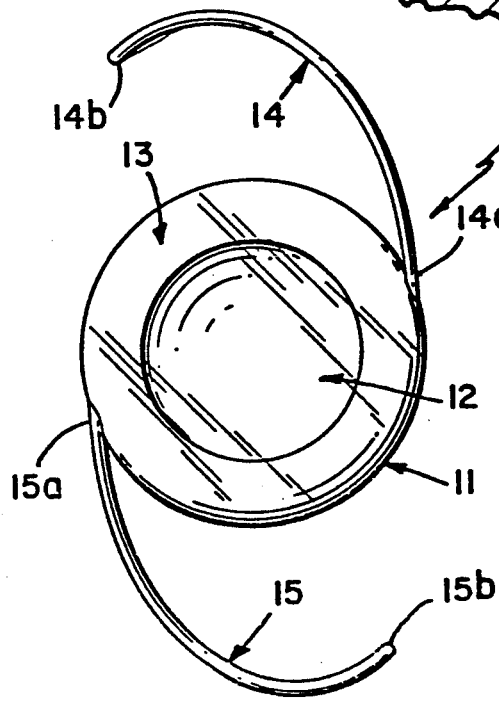
FIG. 2 is a top plan view of the lens of FIG. 1, shown according to a first embodiment of the invention.
Figure 3:
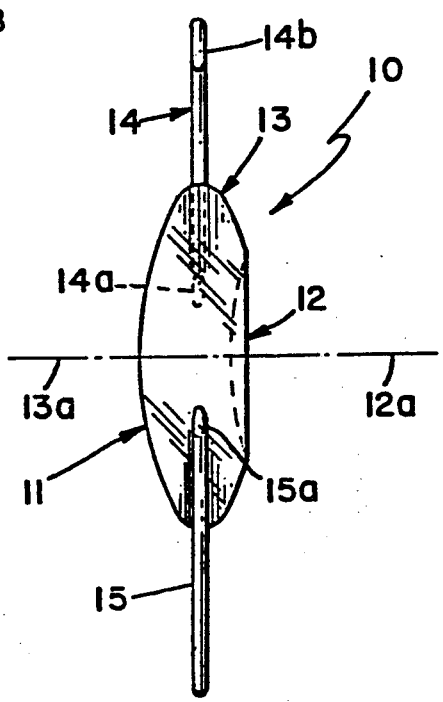
FIG. 3 is a side elevational view of the lens shown in FIG. 1.

Referring to the drawings, wherein like numerals represent like parts throughout the several views, an intraocular lens, designated generally as 10, is shown in FIGS. 1 through 3, with FIG. 2A showing a variation described below. The intraocular lens 10 includes a rigid optical region or lens body 11 which includes a first lens portion or lens 12 cooperatively connected to a second lens portion or lens 13 to form a lens body or optical region 13.

In a preferred embodiment the first lens 12 is an inner lens having an axis 12a. The second lens 13 is an annular lens having an axis 13a. The lens body 11, or optic portion of the intraocular lens 10, is centered and retained within the eye by retaining means such as haptic members 14 and 15 having first ends 14a and 15a and second ends 14b and 15b respectively. The first ends 14a and 15a are cooperatively connected to the lens body 11 by methods well known in the art. Further, the construction and specific configuration of the haptic members 14 and 15 may be any suitable construction, such construction being well known in the art.

In a preferred embodiment, the haptic members 14 and 15, inner lens 12 and annular lens 13 are formed as an integral one-piece structure by a forging and machining process. However, it will be appreciated that the intraocular lens 10 may also be produced by other suitable methods such as injection molding and lathing. As a result, the inner lens 12 and annular lens 13 are substantially non-movable with respect to one another.

The unitary intraocular lens body 11, including the first lens 12 and second lens 13, is made of a biological tolerable and optically suitable material such as polymethylmethacrylate (PMMA). The haptic members 14 and 15 may be made of a flexible, compressible, resilient plastic material such as PMMA or polypropylene, or other materials as well known in the art. Preferably, the entire intraocular lens 10 is of an integral one-piece structure and is made of PMMA.

Preferably the integral one-piece intraocular lens is formed via the previously described method, wherein a mold is first formed with a curved portion having a radius of curvature equal to the higher power lens portion of the arrangement 10. This portion is then polished, and protected with sealant or wax. Next, the mold is ground to provide for the lower power lens portion, i.e. the portion having a larger radius curvature. This portion is then polished. The sealant is removed, and the lens material is pressed into the mold to form the preferred arrangement. In this manner a unitary structure having lens portions of different power can be readily, and accurately, provided. The problems previously discussed with gradient index lens arrangements, are avoided.

The posterior chamber type intraocular lens 10 will typically be utilized following extra capsular cataract extraction. As illustrated in FIG. 1, the lens 10 is implanted in a human eye 40, in the posterior chamber 42 behind the iris 44. Preferably, the cataract has been extracted from the capsular bag 46, leaving intact the posterior wall 46a and an annular flap portion 46b forming a cleft of fornix 46c. The capsular bag 46 is connected to the ciliary muscle in the eye wall 48 via suspensory ligaments 50. Vitreous humor in the region 52 behind the capsular bag 46 is prevented from flowing forward by the posterior wall 46a. It is, of course, understood that the present invention may also be used in the anterior chamber of the eye 40.

The intraocular lens 10 may serve as a bifocal vision system, with one lens 12 for reading and the other lens 13 for distant viewing. As shown in the preferred embodiment, the axis 12a of the inner lens 12 is coaxial with the axis 13a of the annular lens 13. However, it is understood that the certain principles of the present invention will also be applicable where the axes 12a and 13a are not coaxial. The different portions 12 and 13 will be understood to have different radii of curvature.

Many prior art methods of providing bifocal vision systems, such as bifocal glasses, are exclusive; meaning one can either read or look in the distance. Generally, there is a blurred region in between, which is awkward. With the present application this would not be the case. The first lens portion has a focal length that is for viewing near objects and the second lens portion has a focal length that is for viewing distant objects. Such a combination of lenses will produce two images on the retina which are superimposed. Always, one of the two images will appear blurred. If an object up close is viewed, the image produced through the second lens will appear blurred; or, if the object is viewed at a distance, the image through the first lens will appear blurred. The user's brain can select the sharper image for evaluation.

In a preferred embodiment, as shown in the figures, the first lens 12 is a center lens having a focal length for reading and the second lens 13 is an annular ring shaped lens having a focal length for distant viewing. The area of each lens 12 and 13 will ideally be computed individually for each patient, depending upon the patient's iris reflexes, as described more fully hereafter. In actual practice, a whole series of lenses would probably be provided, having different corrective properties, so that an appropriate lens could be selected for any given patient.

In one of the parent cases, it was indicated that preferably the area of the first lens 12 would be from approximately 30% to 50% of the area of the lens body 11. Further, it was indicated as preferred that the first lens 12 be approximately 40% of the total area of the lens body 11 or, otherwise stated, the area of the first lens 12 be approximately equal to the area of the second lens 13. This is shown in FIG. 2.

A preferred arrangement outside of the above-stated range has been found. FIG. 2A shows an arrangement which is substantially identical to FIG. 2 in substance, but for the relative sizes of the lens portions 12' and 13', to indicate the alternate and preferred possibility. For this arrangement, it will generally be preferred that the annular portion have a diameter of about 6.0 to about 7.0 millimeters while the inner portion has a diameter of about 1.8 to about 2.2 millimeters. Thus, the area of the first lens portion is between about 6% and 14% of the combined areas of the first and second lens portions. Most preferably, when the inner portion is the near vision portion, it has a diameter of less than 2 mm. A reason for this is that interference between the two projected images will be less likely. That is, when the wearer reads, light can be adjusted to be relatively bright, the light reflected off the page will be fairly intense, and the iris will contract at least partially blocking the distance vision portion. In distance viewing, the light intensity will generally be lower, and the iris more opened. A relatively small image projected by the near vision portion will be more easily discarded by the brain. In FIG. 2A reference numerals 10', 11', 12', 13', 14', 14a', 15' and 15a' indicate parts generally analogous, in form and function, to parts 10, 11, 12, 13, 14, 14a, 15 and 15a respectively.

It is also foreseen that the desired relative powers between the two lens portions may vary from patient to patient. Generally, for most uses an operable embodiment will have a corrective power of about +15 to about +25 diopters, for the outer lens portion, the portion used for distance viewing; and, a corrective power of about +2 to about +4 diopters larger than the outer lens portion for the inner portion, i.e. that portion used for near viewing. For preferred posterior lens implants, preferably the add on will be at least +3 diopters, or the lens will not focus, in typical uses. Most preferably, the add on is at least +3.5 diopters.

If a distant object is viewed in moderately bright illumination, the iris 44 will be open and the image created by the annular lens 13 (which is sharp) will overpower the blurred and also less bright image created by the inner lens 12. The overpowering process is made possible by the fact that blurred edges are less intense than sharp edges, and by the way the image evaluation system of the brain works.

Reading activity usually takes place indoors, and bright illumination can readily be applied. The iris 44 will close, and the area of the annular lens 13 will be reduced so that the image of the inner lens 12 (which is now sharp) will overpower the blurred, less bright, image generated by the annular lens 13. Therefore, by the management of the intensity of the images, as is accomplished in the present invention, there can be two superimposed images one of which is blurred and one of which is sharp. The brain's evaluation system will accordingly see the sharp image. The image evaluation system of the brain searches for sharp edges and, once it finds a sharp edge, it exaggerates the edge. Therefore, generally, as long as the blurred image is weaker in intensity that the sharp one, the brain will evaluate the images and "see" the sharp image.

It is understood that any suitable combination such as plano-convex, biconcave, meniscus or other combination of lenses may be used with either an add on center or a distance on center to provide for the inner lens 12. It is necessary for one skilled in the art to make a suitable combination of such lenses to provide for a focal length for one of the lenses 12 or 13 for distance reading and a focal length for the other of the lenses 12 or 13 having a focal length for viewing near objects, preferably with both of the lenses having a positive power.

Another embodiment of the present invention is shown in FIGS. 2-2. This lens would also be positioned in the eye as shown in FIG. 1. The second embodiment of the implantable intraocular lens 60 includes a rigid bifocal optical region or lens body 61 which includes a first lens portion 62 and a second lens portion 63, the bases of which are coplanar. The lens body 61 has a chord 61a between lens portions 62 and 63. This embodiment is also adapted to be implanted in the posterior chamber, although the concept can be utilized in an anterior chamber lens as well.

Preferably, the unitary optical lens body 61 is substantially circular, the chord 61a is a diameter of the lens body 61 and the lens portions are semicircular. Thus, for this embodiment the first and second lens portions may preferably be of about the same size and the lens portions are substantially non-movable with respect to one another. The powers for the near vision and distance vision sections are preferably as previously described for the first embodiment.

The lens body 61, or optic portion of the intraocular lens 60, is centered and retained within the eye by retaining means such as haptic members 64 and 65 having first ends 64a and 65a and second ends 64b and 65b, respectively. The first ends 64a and 65a are cooperatively connected to the lens body 61 by methods well known in the art. Further, the construction of a specific configuration of the haptic members 64 and 65 may be any suitable construction, such construction being well known in the art.

Preferably, the haptic members 64 and 65, the first lens 62 and second lens 63 are molded as an integral one-piece structure. Most preferably, a method of molding involving a mold made as previously described is used, in order to provide efficient production without the problems involved in producing gradient index lenses. The unitary intraocular lens body 61, including the first lens 62 and second lens 63, is made of a biological tolerable and optically suitable material such as PMMA. The haptic members 64 and 65 may be made of a flexible, compressible, resilient plastic material such as PMMA or polypropylene, or other materials as well known in the art. Preferably, the entire intraocular lens 60 is made of an integral one-piece structure and also is made of PMMA. The intraocular lens 60 may serve as a bifocal vision system, with one lens 62 for reading and the other lens 63 for distant viewing.

As previously discussed, many prior art methods of providing bifocal vision systems, such as bifocal glasses, are exclusive. With the present embodiment this would not be the case. One of the lens portions would have a focal length that is for viewing near objects and the other of the lens portions would have a focal length different from the first lens portion and that is for viewing distant objects. Such a combination of lenses will produce two images on the retina which are superimposed. Always, one of the two images will appear blurred. The eye is constantly scanning the images created on the retina and selectively chooses the image (the sharp one) to see. By having an intraocular lens 60 that is equally split, with the chord 60a being a horizontal diameter, the iris of the eye will always be in position in front of both lens portions 62 and 63 and therefore the retina will always have an image formed on it from both the lens portions 62 and 63. The area of the first lens portion 62 is preferably approximately equal to the area of the second lens portion 63.

Again, when the two lens portions are equal, the chord 61a is substantially a diameter of the lens body 61. However, the chord 61a could be offset from the center without departing from the invention.

As is clearly shown in FIG. 6, the lens body 61 has a planar bottom surface 61b that extends across both the first lens portion 62 and second lens portion 63. The first lens portion 62 has an upper convex surface 62a and the second lens portion 63 has an upper convex surface 63a, the latter one having a different radius of curvature than the first. Reference numeral 66 generally indicates a transition region between the two lens portions which for the preferred embodiment shown, is chord 61a. In FIG. 6 plane 67 represents a division of the lens 61 into its two halves 62 and 63 of different powers. While different radii of curvatures are drawn, the difference is small and hard to see. It will nevertheless be understood to be present.

FIG. 7 is a cross-sectional view of a lens incorporating the present invention taken from a point of view generally analogous to the use for FIG. 1, but showing an alternate thereto. In particular, the lens body of FIG. 7 is shown having a plano-convex structure. That is, it is generally planar on one side and convex on the other. This arrangement may be advantageous, in that it is potentially easier to construct. For the arrangement shown in FIG. 7, the reference numeral 100 generally designates the eye, and the reference numeral 111 the lens. The arrangement will be understood to be analogous to that shown in FIGS. 1-3, but for the utilization for a plano-convex structure for the lens. The near vision portion 112 of the lens may be, for example, of the relative diameter to the distant vision portion 113, as previously described for FIGS. 1-3. In the alternative, that ratio of areas described previously for FIG. 2A, may also, preferably, be used. Desirable corrective factors for the two portions may be as previously indicated; that is, preferably, with the distance portion having a corrective power of between about +15 and +25 diopters, and with the corrective power of the inner, near vision, lens portion preferably having an add on power of between about +3 and about +4 diopters, and more preferably at least about +3.5 diopters.

In FIG. 8 a top plan view of the lens of FIG. 7 is shown. Again, except for the plano-convex structure, the arrangement is analogous to that shown in FIG. 2.

Finally, in FIG. 8A an alternate to the arrangement shown in FIG. 7 and 8 is shown, wherein the inner lens portion 112' is constructed smaller, with respect to the outer lens portion 113'. Specifically, for this arrangement it will generally be preferred that the annular portion have a diameter of about 6.0 to about 7.0 millimeters, while the inner portion has a diameter of about 1.8 to about 2.0 millimeters. Thus, the arrangement is generally analogous to that shown in FIG. 2A, but for the plano-convex structure.

In general, arrangements according to FIGS. 7, 8 and 8A are more readily susceptible to manufacture according to the described method of molding, than are the embodiments of FIGS. 1-6. A reason for this is that molds having a target arrangement providing for an inner concave region of one diameter and an outer concave region of another diameter can be fairly easily ground.

Although the preferred embodiment of the invention is a bifocal lens, it should be understood that one or more additional lenses may be incorporated to correct for different distances.

Other modifications of the invention will be apparent to those skilled in the art in light of the foregoing description. This description is intended to provide specific examples of individual embodiments which clearly disclose the present invention. Accordingly, the invention is not limited to these embodiments or to the use of elements having specific configurations and shapes as presented herein. All alternative modifications and variations of the present invention which follow in the spirit and broad scope of the appended claims are included.

We claim:

1. A rigid intraocular lens implant adapted for use as an artificial lens implant in a posterior chamber of an eye; said intraocular lens comprising:
   (a) means for non-movably retaining said lens implant within a posterior chamber of a user's eye; and,
   (b) a lens body comprising a material having a first index of refraction and substantially no index of refraction gradient therein; said lens body having a first circular lens portion and a second annular lens portion, said second annular lens portion surrounding said first circular lens portion;
      (i) said first lens portion comprising a portion of said lens body having said first index of refraction and a first radius of curvature defining a first optical power;
      (ii) said second lens portion comprising a portion of said lens body having said first index of refraction and a second radius of curvature defining a second optical power;
      (iii) said second lens portion being constructed and arranged for viewing relatively distant objects and having an optical power of between about +15 and about +25 diopters;
      (iv) said first lens portion being constructed and arranged for viewing relatively near objects and having: a power of at least +3.0 diopters greater than said second lens portion; and, a diameter of no greater than about 2.0 mm.

2. A lens implant according to claim 1 wherein said first lens portion has an area of between about 6% and 14% of a total combined area of said first and second lens portions.

3. The intraocular lens according to claim 1 wherein:

(a) said first lens portion defines a central axis of symmetry; and,
(b) said second lens portion defines a central axis of symmetry substantially coaxial with said central axis of symmetry defined by said first lens portion.

* * * * *